United States Patent
Huh

(10) Patent No.: US 8,049,151 B2
(45) Date of Patent: Nov. 1, 2011

(54) DIGITAL TYPE ANTI-GLARE DEVICE USING TOUCH AND METHOD OF CONTROLLING THE SAME

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 344 days.

(21) Appl. No.: 12/496,716

(22) Filed: Jul. 2, 2009

(65) Prior Publication Data

US 2010/0007938 A1    Jan. 14, 2010

(30) Foreign Application Priority Data

Jul. 11, 2008    (KR) .................. 10-2008-0067470

(51) Int. Cl.
*G01J 1/32* (2006.01)
*G02F 1/1335* (2006.01)

(52) U.S. Cl. ............. 250/205; 250/201.1; 349/14; 2/8.2

(58) Field of Classification Search .......... 250/205, 250/215, 216, 201.1, 214 R; 349/13, 14; 345/7, 8; 2/8.2

See application file for complete search history.

(56) References Cited

U.S. PATENT DOCUMENTS

| | | | |
|---|---|---|---|
| 6,225,316 B1 | 5/2001 | Bos et al. | |
| 6,483,090 B1 | 11/2002 | Bae | |
| 6,614,409 B1 * | 9/2003 | Bae | .................................. 345/8 |
| 7,470,880 B2 | 12/2008 | Huh | |
| 7,755,019 B1 * | 7/2010 | Hamilton et al. | ......... 250/214 R |
| 2007/0131845 A1 | 6/2007 | Huh | |

FOREIGN PATENT DOCUMENTS

| | | |
|---|---|---|
| KR | 10-2005-0095515 | 9/2005 |
| KR | 10-2007-0066536 | 6/2007 |

* cited by examiner

*Primary Examiner* — Kevin Pyo
(74) *Attorney, Agent, or Firm* — Cantor Colburn LLP

(57) ABSTRACT

Disclosed is a digital type anti-glare device capable of conveniently performing input, operation and adjustment, and a method of controlling the same. The digital type anti-glare device includes a touch sensor input unit recognizing a shade degree and a grind mode level by direct selective operation or adjustment of a user as a digital contact signal and inputting the shade degree and the grind model level to the control unit, and an encoder switch input unit recognizing a sensitivity level and an opening delay level by the selective operation or adjustment of the user and inputting the sensitivity level and the opening delay level to the control unit. Accordingly, it is possible to prevent operation failure due to switch contact, dust or humidity or the like by a touch sensor and encoder input and to facilitate input, operation and adjustment even in a state in which an operator wears gloves.

20 Claims, 9 Drawing Sheets

DIGITAL TYPE ANTI-GLARE DEVICE USING TOUCH AND METHOD OF CONTROLLING THE SAME

BACKGROUND OF THE INVENTION

1. Field of the Invention

The present invention relates to an anti-glare device, and more particularly to a digital type anti-glare device capable of displaying a current time, an operation time, a temperature and humidity in a digital manner and facilitating the input of an operator by a touch sensor and encoder input, and a method of controlling the same.

2. Description of the Related Art

Generally, when welding, cutting and grinding are performed, an operator wears a welding mask for blocking strong light and performs an operation, in order to protect the operator's eyes from various types of harmful materials. Accordingly, various convenient and safe electronic welding masks have been developed and used.

FIG. 1 is a perspective view of a conventional protective mask including an anti-glare device.

As shown in FIG. 1, the protective mask 1 including the anti-glare device 2 formed on a front surface thereof reduces illumination intensity of light irradiated to the operator's eyes using an anti-glare plate 5 which is a liquid crystal display (LCD) included in the anti-glare device 2.

That is, a photo-sensor unit 4 such as a photodiode included in the front surface of the anti-glare device 2 senses light generated by a welding and cutting torch. A control circuit included in the anti-glare device 2 controls the anti-glare plate 5 to be darkened such that illumination intensity of light passing through the anti-glare plate is reduced. Accordingly, the operator's eyes are protected by the protective mask 1.

FIG. 2 is a view showing a user interface for adjusting shade, light detection sensitivity and time delay of the conventional anti-glare device.

Referring to FIG. 2, the user interface of the conventional anti-glare device 2 includes a shade adjustment unit 6, a light detection sensitivity adjustment unit 7 and a time delay adjustment unit 8.

The shade adjustment unit 6 adjusts a shade value of the anti-glare plate 5. The shade value refers to a darkness degree of the anti-glare plate 5. If the shade value is adjusted by the shade adjustment unit 6, light transmissivity of the anti-glare plate 5 is adjusted.

The light detection sensitivity adjustment unit 7 adjusts light detection sensitivity of the anti-glare device 2. The light detection sensitivity refers to a value indicating a degree to which the control circuit of the anti-glare device 2 responds to an output signal of the photo-sensor unit 4. If the light detection sensitivity level is high, the control circuit may respond to the output signal with low illumination intensity.

The time delay adjustment unit 8 adjusts time delay of the anti-glare device 2. If the time delay level is low, the control circuit of the anti-glare device 2 rapidly switches the anti-glare plate 5 from a dark state to a bright state when the photo-sensor unit 4 detects that welding is finished. In contrast, if the time delay level is high, it takes much time to switch from the dark state to the bright state.

Generally, in industries associated with the anti-glare device, the shade value level is 5 to 13, the light detection sensitivity level is 0 to 10, and the time delay level is 0 to 10. The user interface of the conventional anti-glare device 2 includes a power switch 9 for turning on/off power, a battery 10 for supplying power, and a low voltage indicator 11 for indicating a low voltage state of the device.

The present applicant developed various anti-glare devices. For example, Korean Patent Application No. 10-2004-0052291 filed on Jul. 6, 2004 discloses an electromagnetic wave detection anti-glare device for detecting electromagnetic waves generated by a welding or cutting torch together with light of high illumination intensity and protecting operator's eyes. Korean Patent Application No. 10-2005-0127844 filed on Dec. 22, 2005 discloses an anti-glare device using voice recognition control, which performs a welding light blocking function using voice recognition technology, conveniently controls various functions without using an operator's hand during welding, and reports a control and operation state vocally, and a method of controlling the same.

However, in the conventional anti-glare device, as shown, the shade adjustment unit 6, the light detection sensitivity adjustment unit 7 and the time delay adjustment unit 8 are manually turned or pressed. There are products in which the adjustment units 6, 7 and 8 are digitalized into push buttons. However, in this case, when the push buttons are used, a display device for displaying a level, such as a Light Emitting Diode (LED) or a Liquid Crystal Display (LCD), is necessary. If the LED is used, a power management problem is caused and thus the pressing of the button may be checked only when the button is pressed. If the LCD is used, a dome-shaped switch panel should be used. In these methods, since switch contact is induced by pressing the push buttons, operation failure of a switch, a knob and a screen window formed of a polycarbonate (PC) material may occur due to abrasion, dust, humidity or the like.

SUMMARY OF THE INVENTION

Therefore, the present invention has been made in view of the above problems, and it is an object of the present invention to provide a digital type anti-glare device capable of preventing operation failure due to switch contact, dust or humidity or the like by a touch sensor and encoder input and facilitating input, operation and adjustment even in a state in which an operator wears gloves, and a method of controlling the same.

It is another object of the present invention to improve convenience of an operation by displaying a current time, an operation time, temperature and humidity in a digital manner and providing a variety of information.

It is another object of the present invention to provide a user operation environment setup and selection function capable of being immediately performed by one touch input by setting an operation environment condition which is frequently used by an operator in advance.

In accordance with an aspect of the present invention, the above and other objects can be accomplished by the provision of a digital type anti-glare device using touch including: an optical detecting unit detecting light generated by a welding or cutting torch; an electromagnetic wave sensing unit sensing electromagnetic waves generated by the welding or cutting torch; an electromagnetic wave detecting unit comparing a resonated signal received from the electromagnetic wave sensing unit with a variably set reference value, when an electromagnetic wave detecting unit start-up signal is applied; a control unit applying the electromagnetic wave detecting unit start-up signal to the electromagnetic detecting unit and monitoring a variation in electromagnetic wave signal received from the output of the electromagnetic wave detecting unit, when light detection is started by the optical detecting unit; a light transmission control unit controlling a variation in light transmissivity of an anti-glare plate according to an output signal of the control unit; a touch sensor input unit recognizing a shade degree and a grind mode level by direct selective operation or adjustment of a user as a digital contact signal and inputting the shade degree and the grind model level to the control unit; and an encoder switch input unit recognizing a sensitivity level and an opening delay level by the selective operation or adjustment of the user and inputting the sensitivity level and the opening delay level to the control unit.

The touch sensor input unit may include a case, a window formed on the case and having numerals or characters printed thereon, a Printed Circuit Board (PCB) located below the case and the window and having a conductive metal or a conductive material mounted or printed therein at a predetermined interval, and an electrode plate formed on the PCB and sending a contact signal to the control unit in response to static electricity of a human body when a finger of the human body approaches or touches the electrode plate.

The encoder switch input unit may be an encoder switch simultaneously inputting a dial type input signal having a value increased or decreased by clockwise or counter-clockwise rotation, and a push button input signal.

The digital type anti-glare device may further include a current time display unit displaying a current time on a front surface of the anti-glare device, an operation time display unit displaying a daily operation time and an accumulated operation time, and a temperature and humidity display unit displaying the temperature and humidity of a current operation place.

The current time display unit, the operation time display unit and the temperature and humidity display unit may display the current time, the daily and accumulated operation times, and the temperature and humidity on a Light Emitting Diode (LED) screen in the form of numerals or characters in a digital manner, respectively.

The digital type anti-glare device may further include a memory unit setting, inputting and storing an operation environment which is frequently used by the user.

The digital type anti-glare device may further include an operation environment setup and selection unit selecting and executing the operation environment stored in the memory unit.

The digital type anti-glare device may further include an alarm display unit receiving an operation finish time and reporting to the user that the operation finish time is reached using a display device including a buzzer or light, when the operation finish time is reached.

In accordance with another aspect of the present invention, there is provided a digital type anti-glare device using touch including: an optical detecting unit detecting light generated by a welding or cutting torch; an electromagnetic wave sensing unit sensing electromagnetic waves generated by the welding or cutting torch; an electromagnetic wave detecting unit comparing a resonated signal received from the electromagnetic wave sensing unit with a variably set reference value, when an electromagnetic wave detecting unit start-up signal is applied; a control unit applying the electromagnetic wave detecting unit start-up signal to the electromagnetic detecting unit and monitoring a variation in electromagnetic wave signal received from the output of the electromagnetic wave detecting unit, when light detection is started by the optical detecting unit; a light transmission control unit controlling a variation in light transmissivity of an anti-glare plate according to an output signal of the control unit; a touch sensor input unit recognizing a shade degree and a grind mode level by direct selective operation or adjustment of a user as a digital contact signal and inputting the shade degree and the grind mode level to the control unit; an encoder switch input unit recognizing a sensitivity level and an opening delay level by the selective operation or adjustment of the user and inputting the sensitivity level and the opening delay level to the control unit; a current time display unit displaying a current time on a front surface of the anti-glare device; an operation time display unit displaying a daily operation time and an accumulated operation time; a temperature and humidity display unit displaying the temperature and humidity of a current operation place; a memory unit setting, inputting and storing an operation environment which is frequently used by the user; an operation environment setup and selection unit selecting and executing the operation environment stored in the memory unit; and an alarm display unit receiving an operation finish time and reporting to the user that the operation finish time is reached using a display device including a buzzer or light, when the operation finish time is reached.

The touch sensor input unit may include a case, a window formed on the case and having numerals or characters printed thereon, a Printed Circuit Board (PCB) located below the case and the window and having a conductive metal or a conductive material mounted or printed therein at a predetermined interval, and an electrode plate formed on the PCB and sending a contact signal to the control unit in response to static electricity of a human body when a finger of the human body approaches or touches the electrode plate. The encoder switch input unit may be an encoder switch simultaneously inputting a dial type input signal having a value increased or decreased by clockwise or counter-clockwise rotation, and a push button input signal.

According to the digital type anti-glare device and the method of controlling the same of the present invention, it is possible to prevent operation failure due to switch contact, dust or humidity or the like by a touch sensor and encoder input and facilitate input, operation and adjustment even in a state in which an operator wears gloves.

In addition, it is possible to improve convenience of an operation by displaying a current time, an operation time, a temperature and a humidity in a digital manner and providing a variety of information.

In addition, it is possible to provide a user operation environment setup and selection function capable of being immediately performed by one touch input by setting an operation environment condition which is frequently used by an operator in advance.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Reference will now be made in detail to the preferred embodiment of the present invention with reference to the attached drawings. The terms or words used in the specification and claims of the present invention are construed as meanings and concepts conforming to the technical spirit of the present invention on the basis of the principle that the inventors can define the concept of the terms properly to explain their invention with the best method. It is to be understood that the detailed description which will be disclosed along with the accompanying drawings is intended to describe the exemplary embodiment of the present invention, and is not intended to describe a unique embodiment which the present invention can be carried out, so that it should be understood that various equivalents and modifications can exist which can replace the embodiments described in the time of the application.

Figure 1:
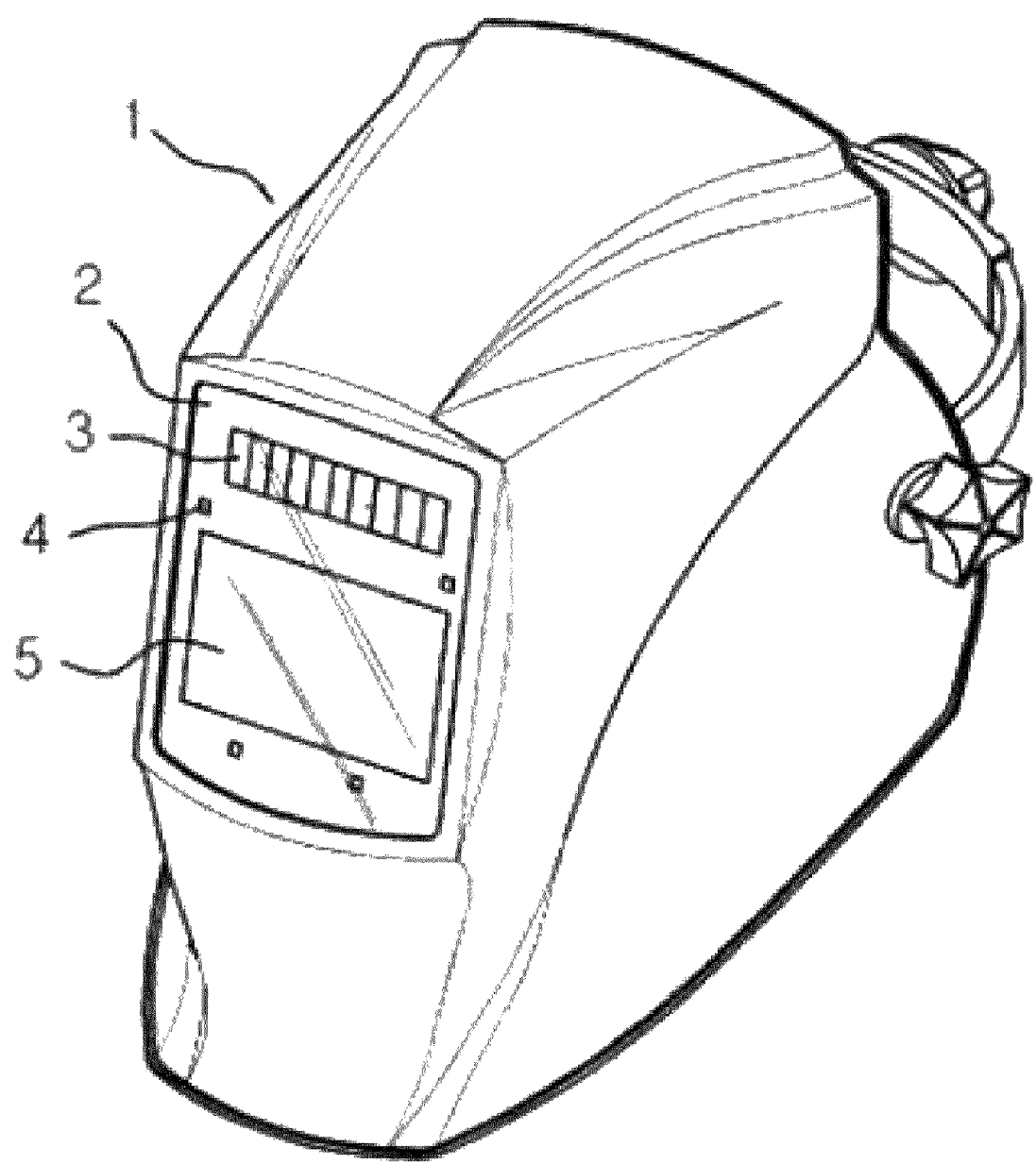
FIG. 1 is a perspective view of a protective mask including a conventional anti-glare device.
Figure 2:
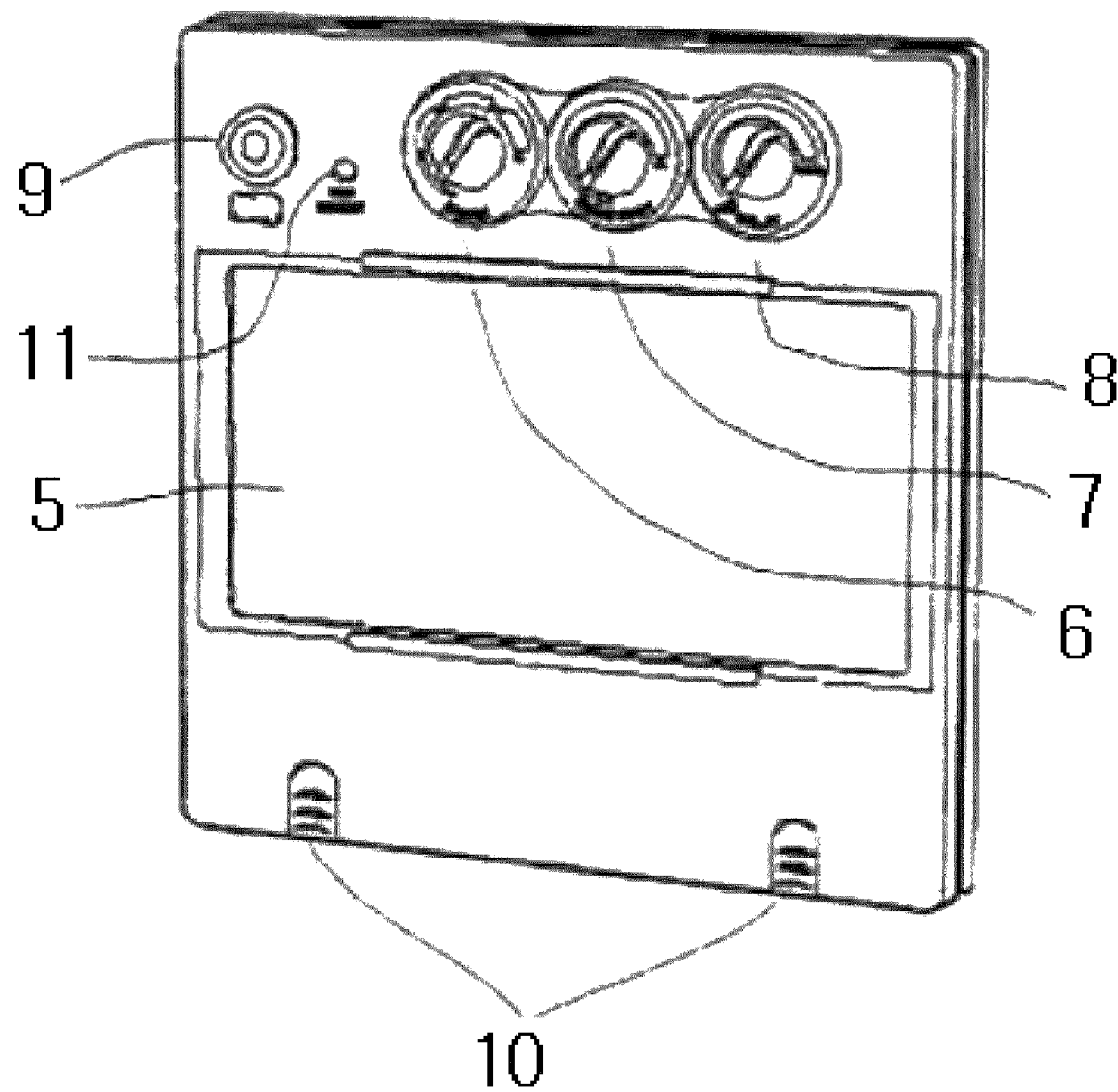
FIG. 2 is a view showing a user interface for adjusting shade, light detection sensitivity and time delay of the conventional anti-glare device.
Figure 3:
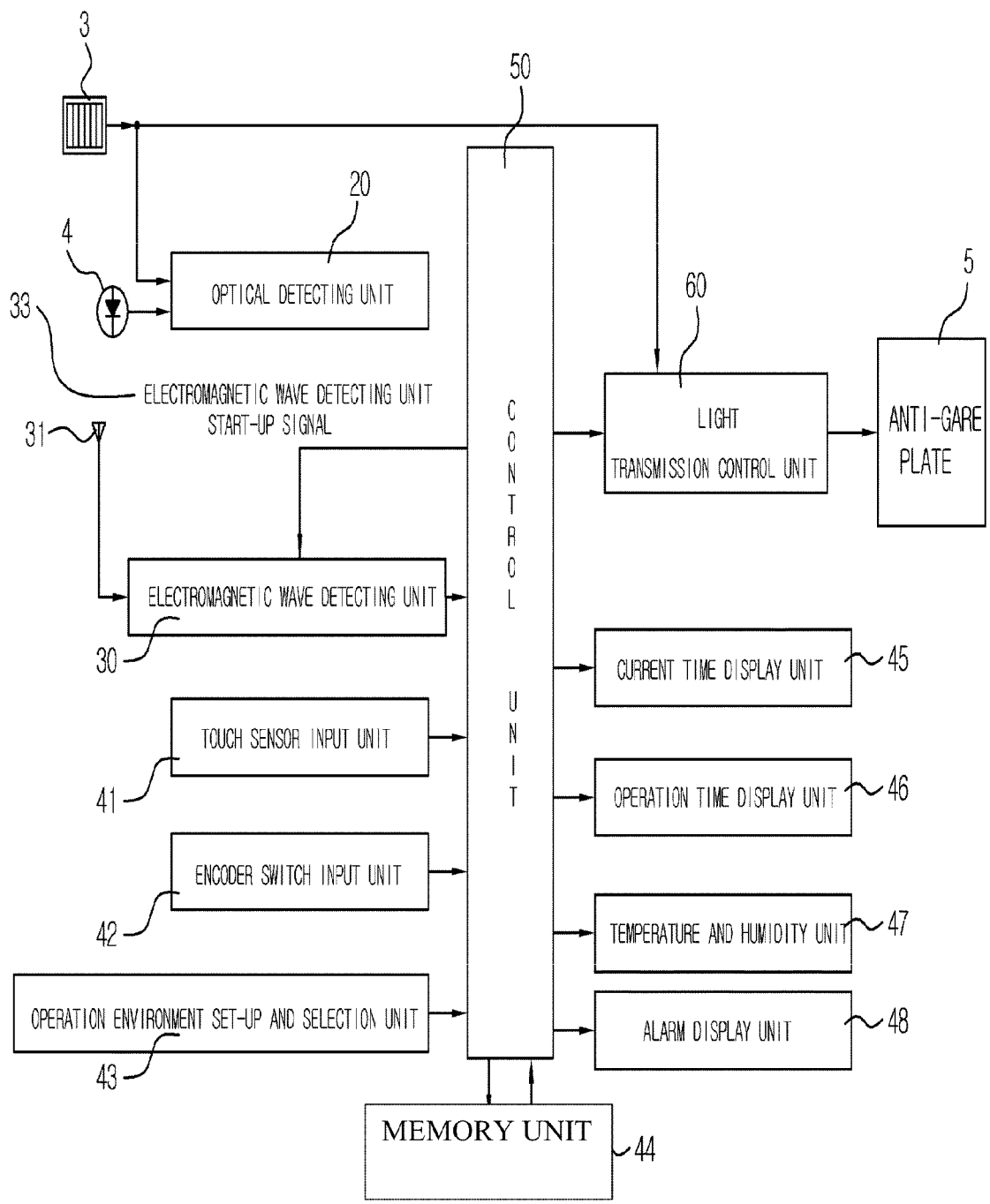
FIG. 3 is a block diagram of a digital type anti-glare device according to an embodiment of the present invention.
Figure 4:
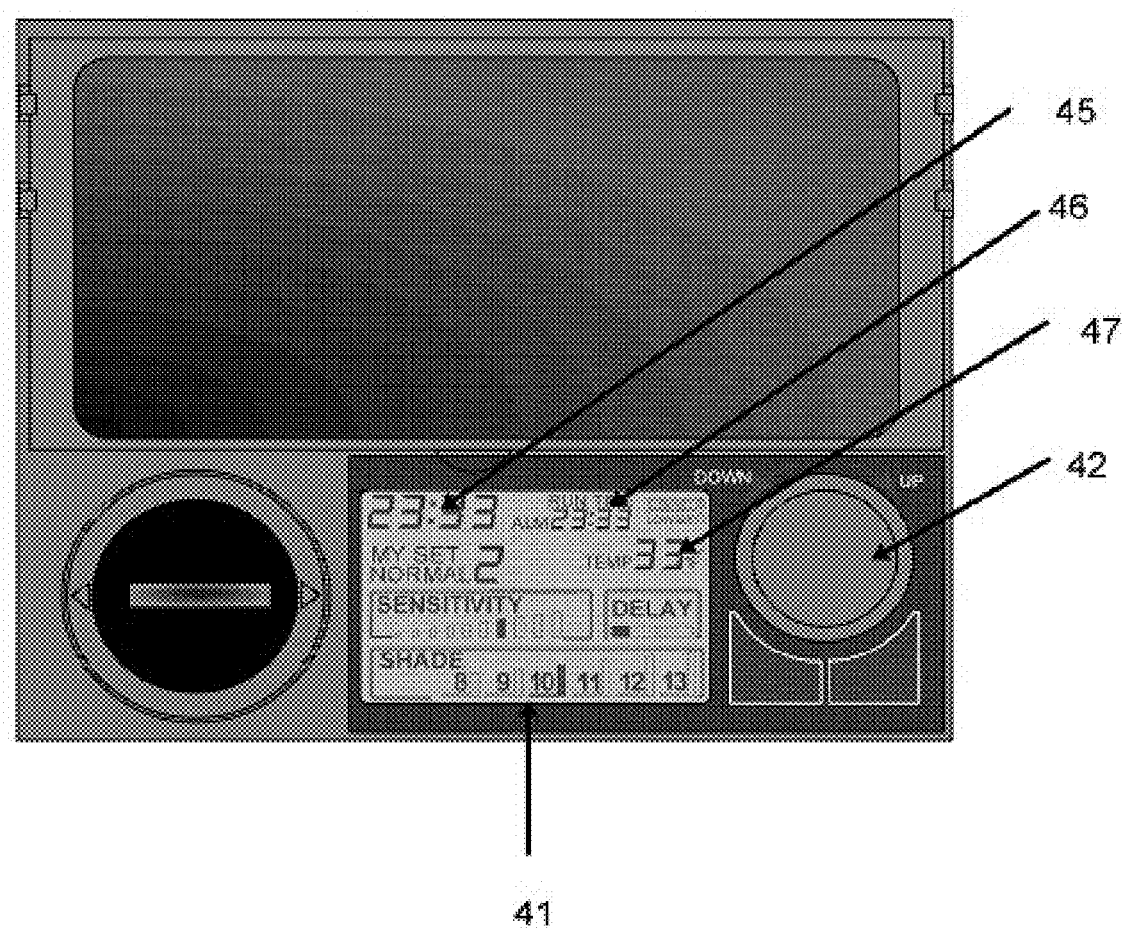
FIG. 4 is a front view of the digital type anti-glare device according to the embodiment of the present invention.

FIG. 3 is a block diagram of a digital type anti-glare device according to an embodiment of the present invention, and FIG. 4 is a front view of the digital type anti-glare device according to the embodiment of the present invention.

As shown, the device according to the present invention includes an optical detecting unit 20, an electromagnetic wave detecting unit 30, an electromagnetic wave sensing unit 31, a touch sensor input unit 41, an encoder switch input unit 42, an operation environment setup and selection unit 43, a memory unit 44, a current time display unit 45, an operation time display unit 46, a temperature and humidity display unit 47, a control unit 50 and a light transmission control unit 60.

The optical detecting unit 20 detects light generated by a welding or cutting torch and includes a filter and an amplifier. The optical detecting unit 20 compares the signal received from a photo-sensor 4 with the output of a solar battery 3 and detects a variation in light quantity.

The electromagnetic wave detecting unit 30 detects electromagnetic waves generated by the welding or cutting torch. The electromagnetic wave detecting unit 30 compares a resonated and filtered signal output from an electromagnetic wave sensing unit 31, which senses the electromagnetic waves generated by the welding or cutting torch of an operator, with a predetermined reference value so as to detect electromagnetic waves having a specific bandwidth.

The control unit 50 applies an electromagnetic wave detecting unit start-up signal 33 to the electromagnetic wave detecting unit 30 and monitors a variation in electromagnetic signal received from the electromagnetic wave detecting unit, when optical detection is started by the optical detecting unit 20.

The light transmission control unit 60 controls a variation in light transmissivity of an anti-glare plate 5 according to the output signal of the control unit 50.

The present invention includes a touch sensor input unit 41 and an encoder switch input unit 42 as a digital adjustment unit which allows a user to adjust a shade level, a light detection sensitivity level, a time delay level and an electromagnetic wave detection sensitivity level.

In detail, the touch sensor input unit 41 directly selects, operates or adjusts a shade degree and a grind mode level by the operation of the user, and inputs the shade degree and the grind mode level to the control unit 50.

The encoder switch input unit 42 selects, operates or adjusts a sensitivity level and an opening delay level by the operation of the user and inputs the sensitivity level and the opening delay level to the control unit 50.

The operation environment setup and selection unit 43 sets an operation environment which is frequently used by the user and inputs and stores the operation environment in the memory unit 44 or selects and executes the operation environment stored in the memory unit 44.

The current time display unit 45 displays a current time on a front surface of the anti-glare device, the operation time display unit 46 displays a daily operation time and an accumulated operation time, and the temperature and humidity display unit 47 displays the temperature and the humidity of a current operation place.

The current time display unit 45, the operation time display unit 46 and the temperature and humidity display unit 47 display the current time, the daily and accumulated operation times, and the temperature and humidity on an LCD screen in the form of numerals or characters in a digital manner, respectively.

Hereinafter, the preferred embodiment of the present invention will be described in detail.

First, the user directly selects, operates or adjusts the shade degree and the grind mode level using the touch sensor input unit 41 so as to input the shade degree and the grind mode level to the control unit 50. In addition, the user selects, operates or adjusts the sensitivity level and the opening delay level using the encoder switch input unit 42 so as to input the sensitivity level and the opening delay level to the control unit 50.

Thereafter, the optical detecting unit 20 detects welding light using the signal received from the photo-sensor 31 and, more particularly, detects the light generated by the welding or cutting torch.

Thereafter, the control unit 50 sets a reference value for controlling the detection sensitivity of the optical detecting unit 20 according to an input value of the user, sets the operation delay time and the light transmission density of the anti-glare plate 5, determines that the detected light is the welding light if the quantity of light detected by the optical detecting unit 20 is equal to or greater than a predetermined reference value, and operates the light transmission control unit 60.

Accordingly, the light transmission control unit 60 operates the anti-glare plate 5 according to the light transmission density set by the control unit 50 and controls the light transmissivity to a predetermined value or less.

The current time display unit 45 displays the current time on the front surface of the anti-glare device, the operation time display unit 46 displays the daily operation time and the accumulated operation time, and the temperature and humidity display unit 47 displays the temperature and the humidity of the current operation place. The current time display unit 45, the operation time display unit 46 and the temperature and humidity display unit 47 display the current time, the daily and accumulated operation times, and the temperature and humidity on the LCD screen in the form of numerals or characters in the digital manner, respectively.

In addition, the electromagnetic wave sensing unit 31 senses the electromagnetic waves generated by the welding or cutting torch, and the electromagnetic wave detecting unit 30 compares the resonated signal received from the electromagnetic wave sensing unit 31 with the variably set reference value.

Accordingly, the control unit 50 operates the light transmission control unit 60 according to a voice command of the user, monitors a variation in electromagnetic wave signal from the output of the electromagnetic detecting unit 30, and controls the operation state.

In addition, the current time, the operation time, the temperature and the humidity are displayed in the digital manner. The operator can conveniently perform input, operation and adjustment while wearing gloves using the touch sensor and the encoder input.

In addition, the operator may set an operation environment condition, which is frequently used, in advance and immediately perform the operation by one touch input.

Figure 5:
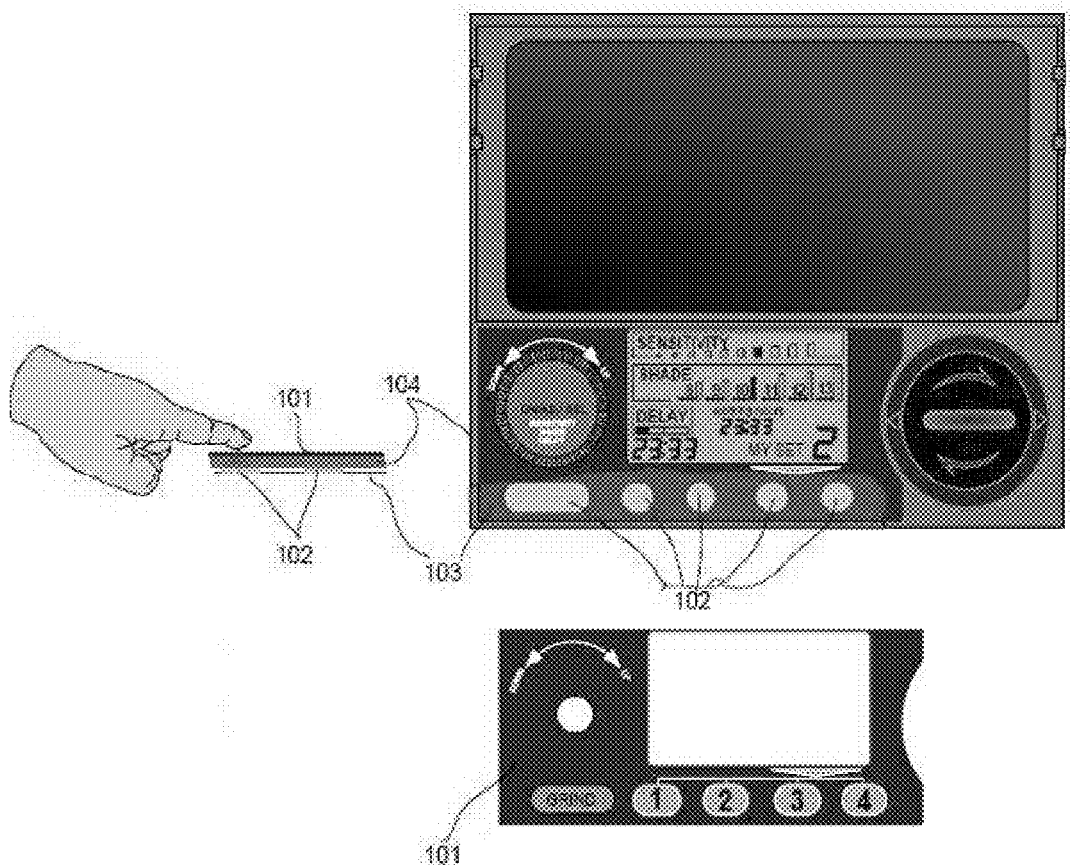
FIG. 5 is a view showing an embodiment of a touch sensor input unit according to the present invention.

FIG. 5 is a view showing an embodiment of the touch sensor input unit according to the present invention.

As shown, the touch sensor input unit 41 according to the present embodiment includes a window 101, an electrode plate 102, a Printed Circuit Board (PCB) 103, and a case 104.

In the touch sensor input unit 41, a conductive metal or a conductive material is mounted or printed on the PCB 103 at a predetermined interval so as to be disposed below the window 101 and the case 104. When a finger of a human body approaches or touches the electrode plate 102, the electrode plate 102 sends a signal to the control unit 50 in response to static electricity of the human body.

The window 101 is formed of a flat non-conductive material and has characters or special symbols printed or craved in a polycarbonate (PC) or plastic material.

In the present invention, since the touch sensor input unit is not operated by pressing but is operated by touch or approach, corrosion is not generated due to abrasion of the switch and humidity.

In addition, since the operator operates the touch sensor input unit while wearing thick welding gloves, it is possible to provide convenience to the user.

In a capacitive method, a capacitive IC or a key pad and a microcomputer with a built-in circuit should be included. Since the present invention is applied by performing reliability testing and other important tests, the static electricity of the human body is used, and the application of a touch switch or a touch sensor in a contact-less manner is defined.

Figure 6:
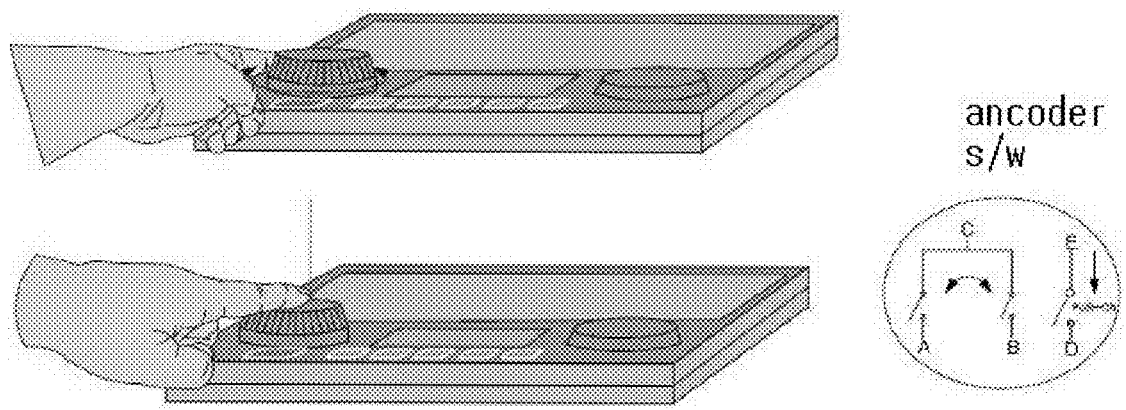
FIG. 6 is a view showing an embodiment of an encoder switch input unit according to the present invention.

FIG. 6 is a view showing an embodiment of the encoder switch input unit according to the present invention.

The encoder switch input unit 42 of the present invention is preferably an encoder switch for simultaneously inputting a dial type input signal having a value increased or decreased by clockwise or counter-clockwise rotation and a push button input signal.

The encoder switch generates pulses having different time differences by the connection between nodes C and A or nodes C and B when rotating in clockwise and counter-clockwise directions as shown in FIG. 6, which change density, sensitivity and a delay time, another level displayed on the display or a graphic level by a programmed controller.

A push button switch which is integrally formed with the encoder switch is located on the central portion of the encoder switch such that other modes or selectable functions can be rapidly selected and changed.

In FIG. 6, since the integral type encoder switch can perform rotation and pressing using the finger of the user, operation convenience and rapid control can be realized. A jog dial which is similar to the encoder switch in function but is different from the encoder switch in rotation may be used.

Figure 7:
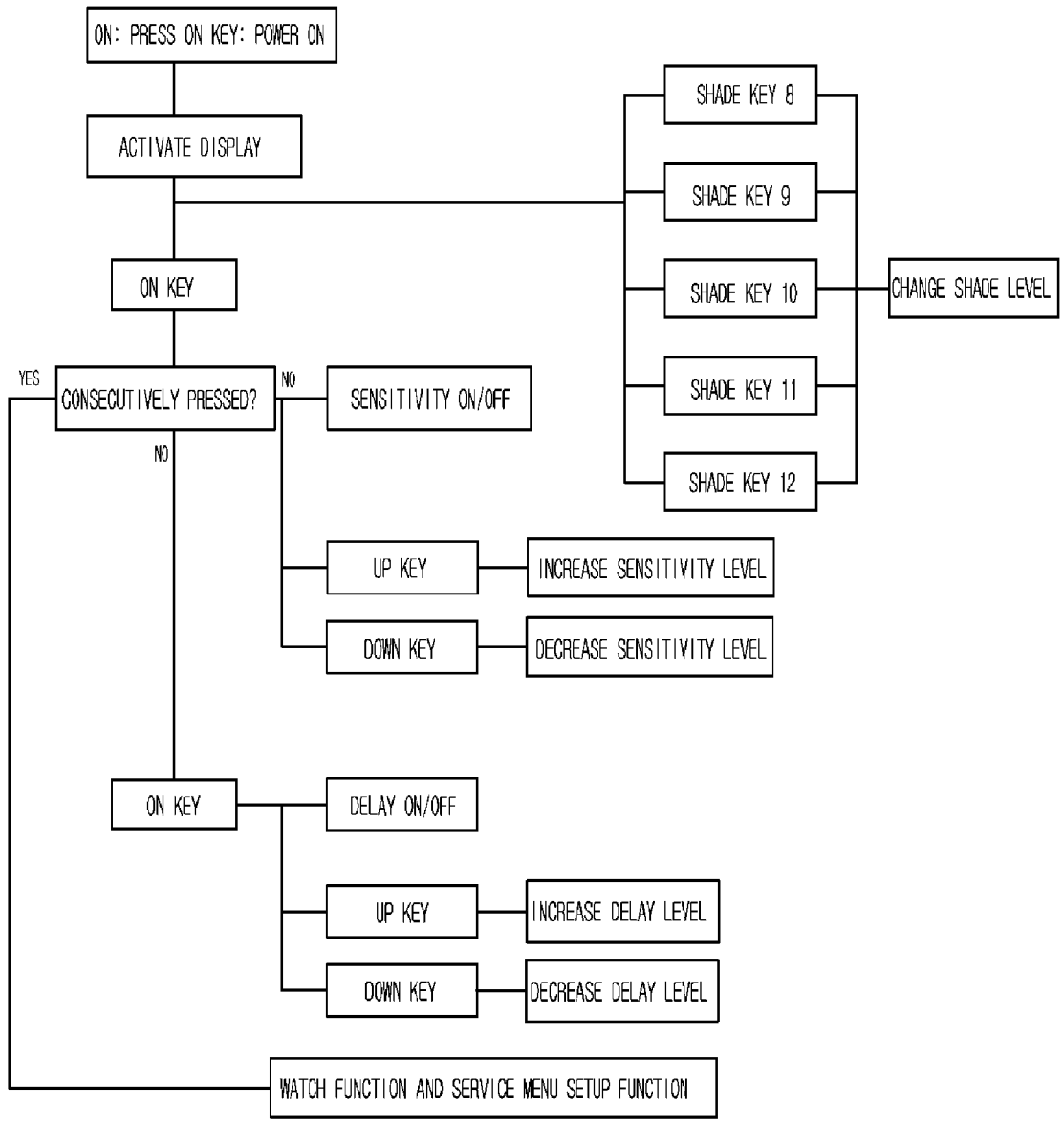
FIG. 7 is a flowchart illustrating a digital type anti-glare method according to an embodiment of the present invention.

FIG. 7 is a flowchart illustrating a digital type anti-glare method according to an embodiment of the present invention.

As shown, in the present invention, power is turned on by pressing an ON key. Thereafter, the display is activated such that a shade level is displayed.

Subsequently, when the ON key is consecutively pressed, a watch function and a service menu setup function are performed.

In contrast, when the ON key is pressed once, the sensitivity display is switched on and off, and an up/down key is adjusted such that the sensitivity level is increased or decreased.

When the ON key is pressed twice, the delay display is switched on and off, and the up/down key is adjusted such that the delay level is increased or decreased.

Figure 8:
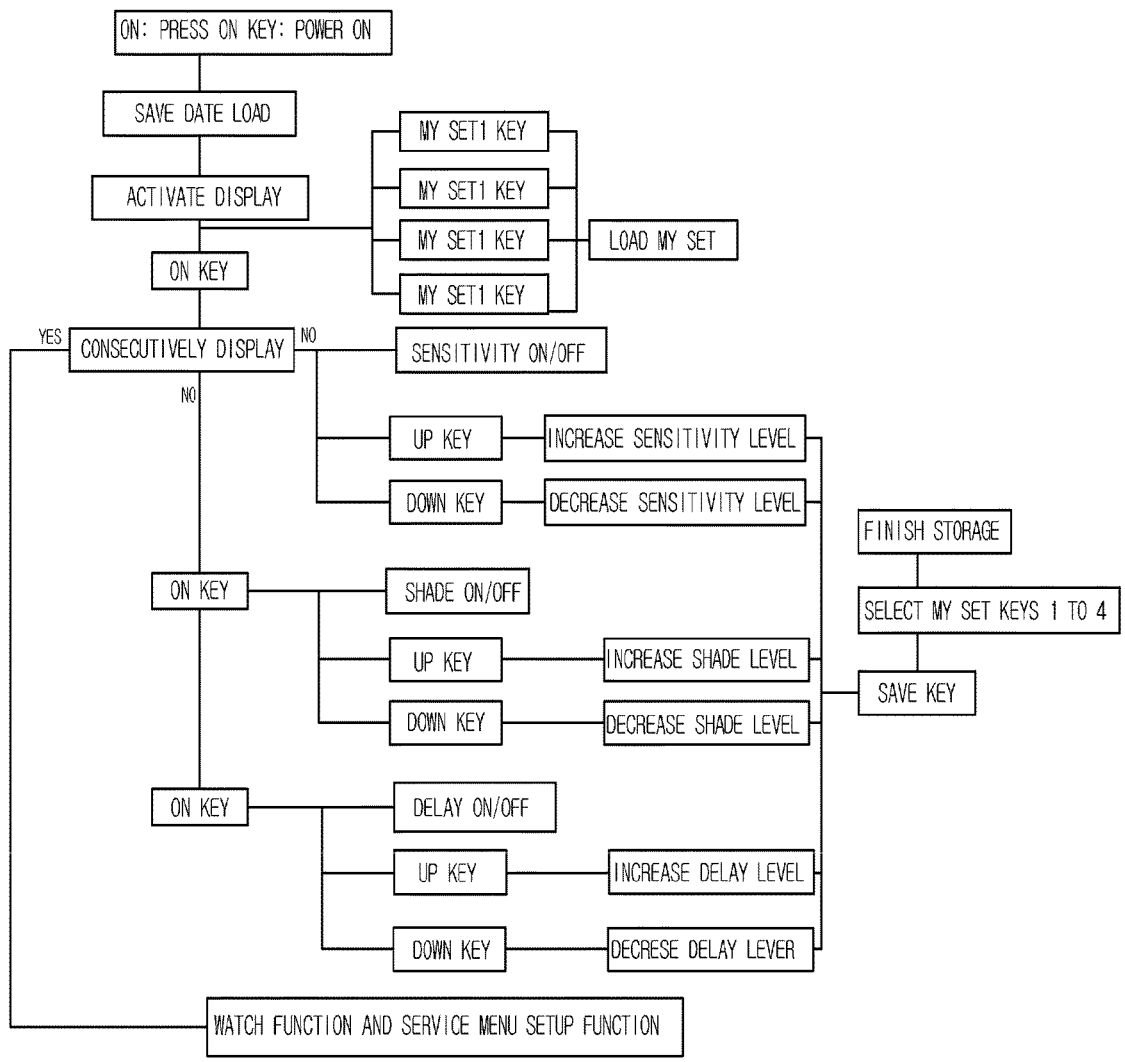
FIG. 8 is a flowchart illustrating a digital type anti-glare method according to another embodiment of the present invention.

FIG. 8 is a flowchart illustrating a digital type anti-glare method according to another embodiment of the present invention.

As shown, in the present invention, when the levels of the sensitivity, density and delay time are selected, a store key is pressed and a "my set" key is pressed, storing is completed. The different levels are stored by this method so as to support rapid countermeasures when the operation environment is changed.

When an alarm display unit of the present invention receives an operation finish time and reports the user that the operation finish time has been reached using a display device including a buzzer or light.

The user alarm display may be implemented by the buzzer, vibration and light, and is operated when the switch is operated or when an alarm is generated.

The switch arrangement of the present invention is realized in a direct manner, and the switch arrangement capable of rapidly changing the level without performing several steps by arranging keys corresponding to divided shade levels in series in the operation of the switch may be realized.

Figure 9:
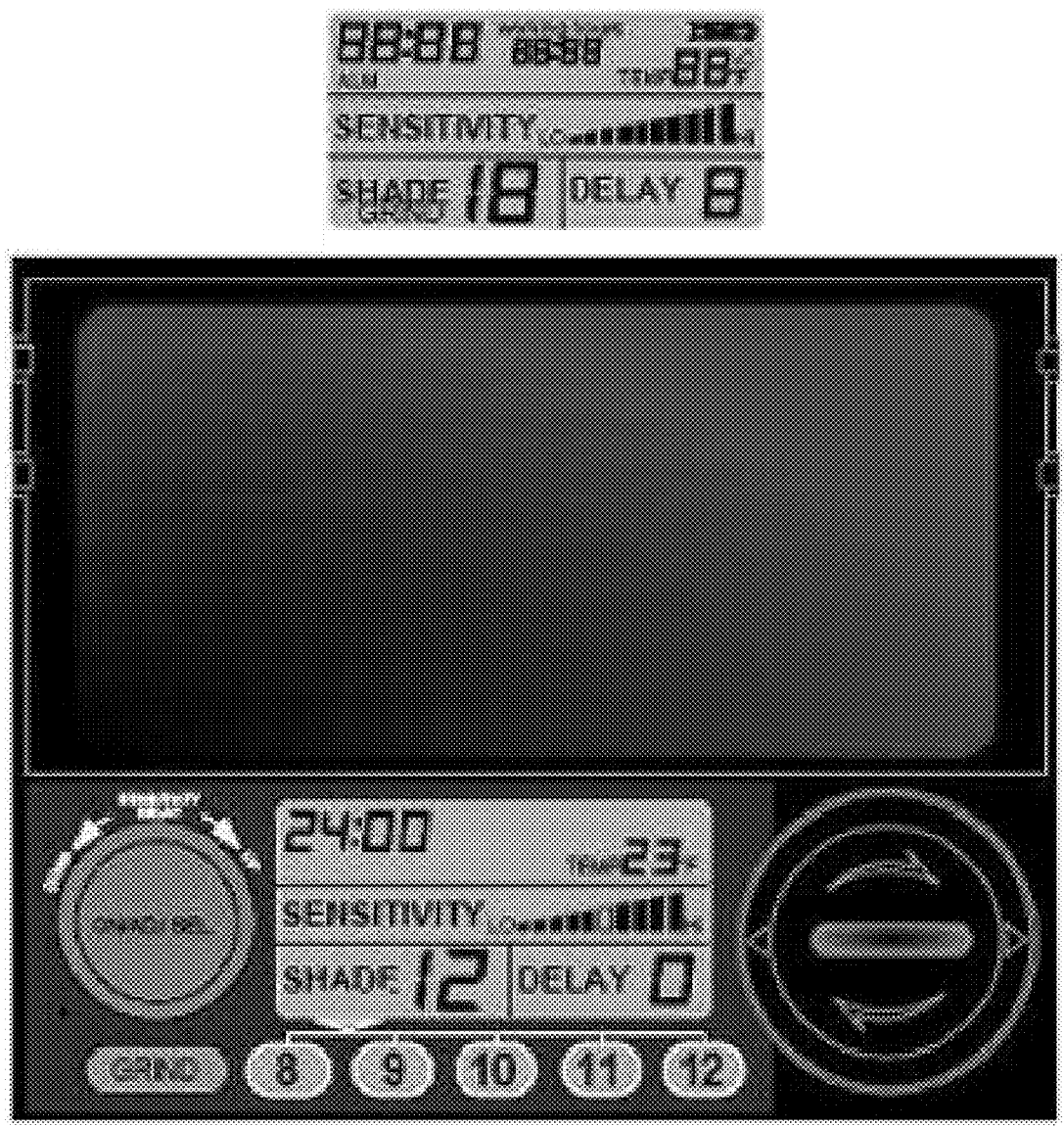
FIG. 9 is a view showing a display unit used in the digital type anti-glare method according to another embodiment of the present invention.

FIG. 9 shows a display unit used in the digital type anti-glare method according to another embodiment of the present invention shown in FIG. 8.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A digital type anti-glare device using touch comprising:
    an optical detecting unit detecting light generated by a welding or cutting torch;
    an electromagnetic wave sensing unit sensing electromagnetic waves generated by the welding or cutting torch;
    an electromagnetic wave detecting unit comparing a resonated signal received from the electromagnetic wave sensing unit with a variably set reference value, when an electromagnetic wave detecting unit start-up signal is applied;
    a control unit applying the electromagnetic wave detecting unit start-up signal to the electromagnetic detecting unit and monitoring a variation in electromagnetic wave signal received from the output of the electromagnetic wave detecting unit, when light detection is started by the optical detecting unit;
    a light transmission control unit controlling a variation in light transmissivity of an anti-glare plate according to an output signal of the control unit;
    a touch sensor input unit recognizing a shade degree and a grind mode level by direct selective operation or adjustment of a user as a digital contact signal and inputting the shade degree and the grind model level to the control unit; and an encoder switch input unit recognizing a sensitivity level and an opening delay level by the selective operation or adjustment of the user and inputting the sensitivity level and the opening delay level to the control unit.

2. The digital type anti-glare device according to claim 1, wherein the touch sensor input unit includes:
   a case;
   a window formed on the case and having numerals or characters printed thereon;
   a Printed Circuit Board (PCB) located below the case and the window and having a conductive metal or a conductive material mounted or printed therein at a predetermined interval; and
   an electrode plate formed on the PCB and sending a contact signal to the control unit in response to static electricity of a human body when a finger of the human body approaches or touches the electrode plate.

3. The digital type anti-glare device according to claim 1, wherein the encoder switch input unit is an encoder switch simultaneously inputting a dial type input signal having a value increased or decreased by clockwise or counter-clockwise rotation, and a push button input signal.

4. The digital type anti-glare device according to claim 1, further comprising:
   a current time display unit displaying a current time on a front surface of the anti-glare device;
   an operation time display unit displaying a daily operation time and an accumulated operation time; and
   a temperature and humidity display unit displaying the temperature and humidity of a current operation place.

5. The digital type anti-glare device according to claim 4, wherein the current time display unit, the operation time display unit and the temperature and humidity display unit display the current time, the daily and accumulated operation times, and the temperature and humidity on a Light Emitting Diode (LED) screen in the form of numerals or characters in a digital manner, respectively.

6. The digital type anti-glare device according to claim 1, further comprising a memory unit setting, inputting and storing an operation environment which is frequently used by the user.

7. The digital type anti-glare device according to claim 6, further comprising an operation environment setup and selection unit selecting and executing the operation environment stored in the memory unit.

8. The digital type anti-glare device according to claim 1, further comprising an alarm display unit receiving an operation finish time and reporting to the user that the operation finish time has been reached using a display device including a buzzer or light, when the operation finish time is reached.

9. A digital type anti-glare device using touch comprising:
   an optical detecting unit detecting light generated by a welding or cutting torch;
   an electromagnetic wave sensing unit sensing electromagnetic waves generated by the welding or cutting torch;
   an electromagnetic wave detecting unit comparing a resonated signal received from the electromagnetic wave sensing unit with a variably set reference value, when an electromagnetic wave detecting unit start-up signal is applied;
   a control unit applying the electromagnetic wave detecting unit start-up signal to the electromagnetic detecting unit and monitoring a variation in electromagnetic wave signal received from the output of the electromagnetic wave detecting unit, when light detection is started by the optical detecting unit;
   a light transmission control unit controlling a variation in light transmissivity of an anti-glare plate according to an output signal of the control unit;
   a touch sensor input unit recognizing a shade degree and a grind mode level by direct selective operation or adjustment of a user as a digital contact signal and inputting the shade degree and the grind mode level to the control unit;
   an encoder switch input unit recognizing a sensitivity level and an opening delay level by the selective operation or adjustment of the user and inputting the sensitivity level and the opening delay level to the control unit;
   a current time display unit displaying a current time on a front surface of the anti-glare device;
   an operation time display unit displaying a daily operation time and an accumulated operation time;
   a temperature and humidity display unit displaying the temperature and humidity of a current operation place;
   a memory unit setting, inputting and storing an operation environment which is frequently used by the user;
   an operation environment setup and selection unit selecting and executing the operation environment stored in the memory unit; and
   an alarm display unit receiving an operation finish time and reporting to the user that the operation finish time has been reached using a display device including a buzzer or light, when the operation finish time is reached.

10. The digital type anti-glare device according to claim 9, wherein:
    the touch sensor input unit includes:
    a case;
    a window formed on the case and having numerals or characters printed thereon;
    a Printed Circuit Board (PCB) located below the case and the window and having a conductive metal or a conductive material mounted or printed therein at a predetermined interval; and
    an electrode plate formed on the PCB and sending a contact signal to the control unit in response to static electricity of a human body when a finger of the human body approaches or touches the electrode plate, and
    the encoder switch input unit is an encoder switch simultaneously inputting a dial type input signal having a value increased or decreased by clockwise or counterclockwise rotation, and a push button input signal.

11. A method of controlling a digital type anti-glare device using touch, which includes an optical detecting unit detecting light generated by a welding or cutting torch, an electromagnetic wave sensing unit sensing electromagnetic waves generated by the welding or cutting torch, an electromagnetic wave detecting unit comparing a resonated signal received from the electromagnetic wave sensing unit with a variably set reference value, when an electromagnetic wave detecting unit start-up signal is applied, a control unit applying the electromagnetic wave detecting unit start-up signal to the electromagnetic detecting unit and monitoring a variation in electromagnetic wave signal received from the output of the electromagnetic wave detecting unit when light detection is started by the optical detecting unit, and a light transmission control unit controlling a variation in light transmissivity of an anti-glare plate according to an output signal of the control unit, the method comprising:
    recognizing a shade degree and a grind mode level by direct selective operation or adjustment of a user as a digital contact signal and inputting the shade degree and the grind model level to the control unit; and recognizing a sensitivity level and an opening delay level by the selective operation or adjustment of the user and inputting the sensitivity level and the opening delay level to the control unit.

12. The method according to claim 11, wherein the inputting of the shade degree and the grind mode level is performed by a window formed on a case and having numerals or characters printed thereon, a Printed Circuit Board (PCB) located below the case and the window and having a conductive metal or a conductive material mounted or printed therein at a predetermined interval, and an electrode plate formed on the PCB and sending a contact signal to the control unit in response to static electricity of a human body when a finger of the human body approaches or touches the electrode plate.

13. The method according to claim 11, wherein the inputting of the sensitivity level and the opening delay level includes simultaneously inputting a dial type input signal having a value increased or decreased by clockwise or counter-clockwise rotation, and a push button input signal by an encoder switch.

14. The method according to claim 11, further comprising:
displaying a current time on a front surface of the anti-glare device;
displaying a daily operation time and an accumulated operation time; and
displaying the temperature and humidity of a current operation place.

15. The method according to claim 14, wherein the current time, the daily operation time, the accumulated operation time, the temperature, and the humidity are displayed on a Light Emitting Diode (LED) screen in the form of numerals or characters in a digital manner.

16. The method according to claim 11, further comprising setting, inputting and storing an operation environment which is frequently used by the user.

17. The method according to claim 16, further comprising selecting and executing the operation environment stored in the storing of the operation environment.

18. The method according to claim 1, further comprising receiving an operation finish time and reporting to the user that the operation finish time has been reached using a display device including a buzzer or light when the operation finish time is reached.

19. A method of controlling a digital type anti-glare device using touch, which includes an optical detecting unit detecting light generated by a welding or cutting torch, an electromagnetic wave sensing unit sensing electromagnetic waves generated by the welding or cutting torch, an electromagnetic wave detecting unit comparing a resonated signal received from the electromagnetic wave sensing unit with a variably set reference value, when an electromagnetic wave detecting unit start-up signal is applied, a control unit applying the electromagnetic wave detecting unit start-up signal to the electromagnetic wave detecting unit and monitoring a variation in electromagnetic wave signal received from the output of the electromagnetic wave detecting unit when light detection is started by the optical detecting unit, and a light transmission control unit controlling a variation in light transmissivity of an anti-glare plate according to an output signal of the control unit, the method comprising:

recognizing a shade degree and a grind mode level by direct selective operation or adjustment of a user as a digital contact signal and inputting the shade degree and the grind model level to the control unit;

recognizing a sensitivity level and an opening delay level by the selective operation or adjustment of the user and inputting the sensitivity level and the opening delay level to the control unit, displaying a current time on a front surface of the anti-glare device;

displaying a daily operation time and an accumulated operation time;

displaying the temperature and humidity of a current operation place, setting, inputting and storing an operation environment which is frequently used by the user;

selecting and executing the operation environment stored in the storing of the operation environment; and receiving an operation finish time and reporting to the user that the operation finish time has been reached using a display device including a buzzer or light, when the operation finish time is reached.

20. The method according to claim 19, wherein:
the inputting of the shade degree and the grind mode level is performed by a window formed on a case and having numerals or characters printed thereon, a Printed Circuit Board (PCB) located below the case and the window and having a conductive metal or a conductive material mounted or printed therein at a predetermined interval, and an electrode plate formed on the PCB and sending a contact signal to the control unit in response to static electricity of a human body when a finger of the human body approaches or touches the electrode plate, and the inputting of the sensitivity level and the opening delay level includes simultaneously inputting a dial type input signal having a value increased or decreased by clockwise or counter-clockwise rotation, and a push button input signal by an encoder switch.

* * * * *